United States Patent [19]
Chia et al.

[11] Patent Number: 5,897,554
[45] Date of Patent: Apr. 27, 1999

[54] STEERABLE CATHETER HAVING A LOOP ELECTRODE

[75] Inventors: Weng-Kwen Raymond Chia, Irvine; Hosheng Tu, Tustin, both of Calif.

[73] Assignee: Irvine Biomedical, Inc., Irvine, Calif.

[21] Appl. No.: 08/813,785

[22] Filed: Mar. 1, 1997

[51] Int. Cl.[6] .................................................. A61N 1/05
[52] U.S. Cl. ................................................ 606/41; 607/122
[58] Field of Search ................................. 600/373, 374; 606/41, 45–47; 607/119, 122

[56] References Cited

U.S. PATENT DOCUMENTS

| | | | |
|---|---|---|---|
| 4,326,530 | 4/1982 | Fleury, Jr. | 606/47 |
| 4,998,975 | 3/1991 | Cohen et al. | 607/122 |
| 5,190,050 | 3/1993 | Nitzsche | 128/772 |
| 5,263,493 | 11/1993 | Avitall | 600/374 |
| 5,281,218 | 1/1994 | Imran | 606/41 |
| 5,336,518 | 8/1994 | Narayanan et al. | 623/1 |
| 5,376,095 | 12/1994 | Kline | 606/47 |
| 5,454,370 | 10/1995 | Avitall | 607/122 |
| 5,458,597 | 10/1995 | Edwards et al. | 606/41 |
| 5,514,130 | 5/1996 | Baket | 606/41 |
| 5,536,267 | 7/1996 | Edwards et al. | 606/41 |
| 5,555,883 | 9/1996 | Avitall | 128/642 |
| 5,643,197 | 7/1997 | Brucker et al. | 606/46 |
| 5,676,662 | 10/1997 | Fleischhacker et al. | 606/41 |

*Primary Examiner*—Jeffrey R. Jastrzab
*Assistant Examiner*—David M. Ruddy

[57] ABSTRACT

An electrophysiology catheter suitable for radiofrequency ablation of cardiac tissues comprises a proximal section, a catheter shaft section and a distal section whereby a distal loop electrode having a temperature sensor and a close-loop temperature control. A conducting wire extends through the lumen and is connected to the loop electrode. The steerable catheter having a loop electrode is inserted into the chambers of the heart to create a continuous, non-linear lesion by supplying radiofrequency energy to said conducting wire.

5 Claims, 4 Drawing Sheets

STEERABLE CATHETER HAVING A LOOP ELECTRODE

FIELD OF THE INVENTION

The present invention generally relates to improved constructions for steerable cardiovascular catheters. More particularly, this invention relates to methods and apparatus for ablating cardiac arrhythmias via a steerable cardiovascular catheter having a loop electrode for ablating intracardiac tissues resulting in a continuous, non-linear lesion.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart. The heart includes a number of normal pathways which are responsible for the propagation of electrical signals from upper to lower chamber necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols which have proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in order to ablate the tissue of arrhythmogenic site or the accessory pathway. By successfully destroying that tissue, the abnormal signal patterns responsible for the tachycardia may be eliminated. However, in the case of atrial fibrillation (AFib), multiple arrhythmogenic sites and/or multiple accessory pathways exist. The conventional catheter with a single ablation tip electrode can not effectively cure the symptoms.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

A catheter utilized in the radiofrequency ablation is inserted into a major vein or artery, usually in the neck or groin area. The tip section of a catheter is referred to here as the portion of that catheter shaft containing the electrode or electrodes which is deflectable. The catheter is then guided into chambers of the heart by appropriate manipulation through the vein or artery. The tip of a catheter must be manipulatable by a physician from the proximal end of the catheter, so that the electrode at the tip section can be positioned against the tissue site to be ablated. The catheter must have a great deal of flexibility in order to follow the pathway of major blood vessels into the heart. It must permit user manipulation of the tip even when the catheter body is in a curved and twisted configuration. The tip section of a conventional electrophysiology catheter that is deflectable usually contains one large electrode about 4 mm in length for ablation purpose. A temperature sensor is usually attached on that electrode.

Imran in U.S. Pat. No. 5,281,218 teaches a needle electrode attached on a catheter for radiofrequency ablation. Though a needle like electrode is beneficial to ablate a tissue point for deep lesions, it is not possible to ablate the tissue in a long continuous non-linear curve or a close-loop circular fashion. For atrial fibrillation treatment, its limitation of a point ablation is obvious.

While a radiofrequency electrophysiology ablation procedure using an existing catheter has had promising results, the tip section of a known catheter usually have only one large electrode for ablation purpose. Recently a non-steerable ablation catheter having multiple large electrodes were introduced to treat the AFib symptoms. The resulting contiguous lesion proves to be a useful, but not optimal, treatment for AFib patients. It is hypothesized that a continuous lesion, rather than a contiguous lesion, is the key for an effective therapy of the cardiac ablation. It is the purpose of this invention to provide a steerable loop electrode to create a continuous non-linear lesion for cardiac ablation.

SUMMARY OF THE INVENTION

The present invention provides an improved steerable catheter which can be used in ablating the arrhythmogenic region instead of an arrhythmogenic point of a patient. This catheter is particularly useful for treating the patients with atrial fibrillation (AFib) indications. In one embodiment, an ablation catheter comprises a catheter shaft whereby a distal tip section having a loop electrode. A conducting wire which is soldered to the loop electrode passes through the shaft into the sub-lumen, followed by passing through the main lumen and thereafter being soldered to a contact pin of the connector at the proximal end. The ablation catheter further comprises a steering mechanism at the handle for controlling the deflection of said loop electrode. Usually a rotating ring or a push-pull plunger is employed in the steering mechanism. The loop electrode configuration can be a diamond shape, a circular or non-circular shape, a double circular shape, an irregular shape, an asymmetrical loop shape, or the like. To maintain the tip section having a loop electrode in a desired shape, a spring or a proper bare wire is inserted inside the sub-shaft as a support. In another embodiment, the steerable ablation catheter comprises the bi-directional deflection of the loop electrode perpendicular to the loop plane. The steerable ablation catheter further comprises a close-loop temperature control mechanism for the loop electrode having a temperature sensor.

In a further embodiment, the catheter of this invention comprises a proximal section, a catheter shaft section with a central lumen, and a distal tip section comprising two parallel sub-shafts each having a sub-lumen whereby each sub-lumen is connected to the main central lumen of the catheter shaft. The far distal end of these two sub-shafts are connected and covered with a loop electrode on the surface of the sub-shafts. The double sub-shafts section with a loop electrode constitutes the tip section of said catheter. Steering wires extending from the handle at the proximal section through the central lumen and the sub-lumens are attached to the distal end of the flat wires inside each sub-shaft. The flat wire extends from the anchoring point in the main shaft to some strategic point in the sub-shaft. The steerability may rely on steering wires extending from the proximal end of a catheter to the tip section, whereby each steering wire provides a mechanism for fine deflecting positioning of one sub-shaft of the loop electrode.

The sub-shafts having a loop electrode are relatively parallel when the tip section is enclosed in a sheath as an introducer. The catheter along with the sheath is inserted into a vein or an artery. After the catheter enters the heart chamber, the tip section is pushed out of the sheath from a pusher at the handle. Thereafter a loop-shape tip unit comprising those two sub-shafts, having a loop electrode onto it, is gradually deployed until the whole section of the sub-shafts is out of the sheath. The loop electrode is deflectable by controlling the steering wires as described above. The loop electrode at the tip section are selected from the group consisting of flexible meshed metal electrodes, flexible coiled metal electrodes, and a combination of the above. The flat wire is preferably made of a metal or a metal alloy having strength, resiliency, and flexibility.

In another embodiment, the steerable catheter comprises a proximal section, a catheter shaft section with a central lumen, and a distal tip section. The distal tip section comprises one inner sub-shaft having a steering wire and a flat wire as steering mechanism, and two peripheral sub-shafts each having a sub-lumen whereby each sub-lumen is connected to the main central lumen of the catheter shaft. The far distal end of these two peripheral sub-shafts are connected and covered with a loop electrode on the surface of said sub-shafts. The peripheral sub-shafts with a loop electrode and the inner sub-shaft constitutes the tip section of said catheter. The distal end of the inner sub-shaft which has a steering mechanism is attached firmly onto the mid-point of the said loop electrode. A steering wire extending from the handle at the proximal section through the central lumen and the sub-lumen of the inner sub-shaft is attached to the distal end of a flat wire inside the inner sub-shaft. The flat wire extends from the anchoring point in the main shaft to some strategic point in that sub-shaft. The steerability may rely on the steering wire extending from the proximal end of a catheter to the tip section, whereby the steering wire provides a mechanism for deflecting positioning of the inner sub-shaft and subsequently deflect the loop electrode because of its joint to the loop electrode.

In one embodiment, the flexible meshed metal electrode is constructed of flexible meshes which wrap over the joint portion of said catheter sub-shafts. In another embodiment, the flexible coiled metal electrode is constructed of flexible coiled wires or coiled springs that wrap over the joint portion of the catheter shaft. In the particular embodiment, the length of the flexible loop electrode is 4 mm or longer, preferably 10 to 100 mm. In an alternate embodiment, a short section of a conventional rigid band electrode can be located at either end of the loop electrode of this invention. The material for the loop electrode may consist of metals such as platinum, iridium, gold, silver, stainless steel, Nitinol, or an alloy of their mixture.

In a still further embodiment, the loop electrode is formed of a conducting material without catheter shaft. The loop electrode in this embodiment is formed of a flexible metal that can be retracted into the sheath during inserting and withdrawing of the said catheter system. The loop electrode can be pre-shaped so that when extended from the sheath, it forms a loop in a plane different from the regular plane involving the catheter shaft.

In an exemplary embodiment, the means for deflecting the distal portion of the catheter comprises at least one steering wire along with a flat wire. Said steering wires are attached to radially offset locations at the distal end of the deflectable portion of the catheter sub-shaft whereas at least a flat wire radially offset the steering wires, and means at the proximal end of the shaft for selectively applying tension to the steering wires to cause deflection of the deflectable tip section. In some cases, the function of a flat wire can be substituted by a spring coil that is stationary at its proximal end with respect to the sub-shaft.

In still another example, the distal portion of the shaft includes at least three radially offset lumens, and wherein the two steering wires and one flat wire are disposed in the central lumen of the catheter shaft over a proximal portion thereof; the two steering wires disposed in the radially offset lumens over the distal portion thereof and the flat wire disposed in the central lumen.

Usually the means for selectively applying tension comprises a handle, and means for applying tension to the steering wire comprises a rotatable ring or a push-pull button disposed on the handle, the ring or button being coupled to the proximal end of a steering wire. A variety of other tension applying mechanisms, such as joy sticks, may also be employed.

In order to provide increased torsional rigidity to the catheter shaft, the shaft material preferably comprises a polymeric tube having a Durometer in the range from 30D to 90D, usually from 40D to 65D. Preferably, the shaft will have a composite structure including a base layer of a relatively low Durometer material, a stiffening layer, for example, metal braid or coil, and an outer layer comprising the biocompatible polymeric material or the material that may render itself biocompatible by surface treatment. To enhance biocompatibility, the catheter shaft further comprises surface coating of heparin, or the like on the surface of the catheter shaft. It is hypothesized that the coated heparin forms a barrier, while not releasing heparin from said surface, between the blood and the catheter surface to enhance biocompatibility during electrophysiology procedures. In a further embodiment, an ablation catheter further comprises surface treatment of low surface energy substrates, such as Teflon® type fluorinated polymers, to mitigate blood coagulation during high energy ablation. Fluorinated polymer can be deposited on the shaft surface via plasma coating technology or the like.

A method for operating a steerable ablation catheter having a loop electrode at its tip section within a heart chamber comprises percutaneously introducing the catheter with a sheath through a blood vessel to the heart chamber, wherein the loop electrode is deployed by pulling back the sheath of the catheter shaft and forming the desired loop pre-shape; deflecting the distal section of the catheter about a transverse axis to position the loop electrode near a target region on an interior wall of the heart chamber; intimately contacting the loop electrode with the intracardiac tissue; and applying radio frequency energy to the target location through the loop electrode of this invention. In a further embodiment, apply microwave energy or ultrasound energy to the target location.

The method and apparatus of the present invention have several significant advantages over known catheter or ablation techniques. In particular, the loop electrode of a steerable ablation catheter of this invention may result in a continuous, non-linear lesion which is highly desirable in the AFib treatment.

DETAILED DESCRIPTION OF EXEMPLARY EMBODIMENTS

Figure 1:
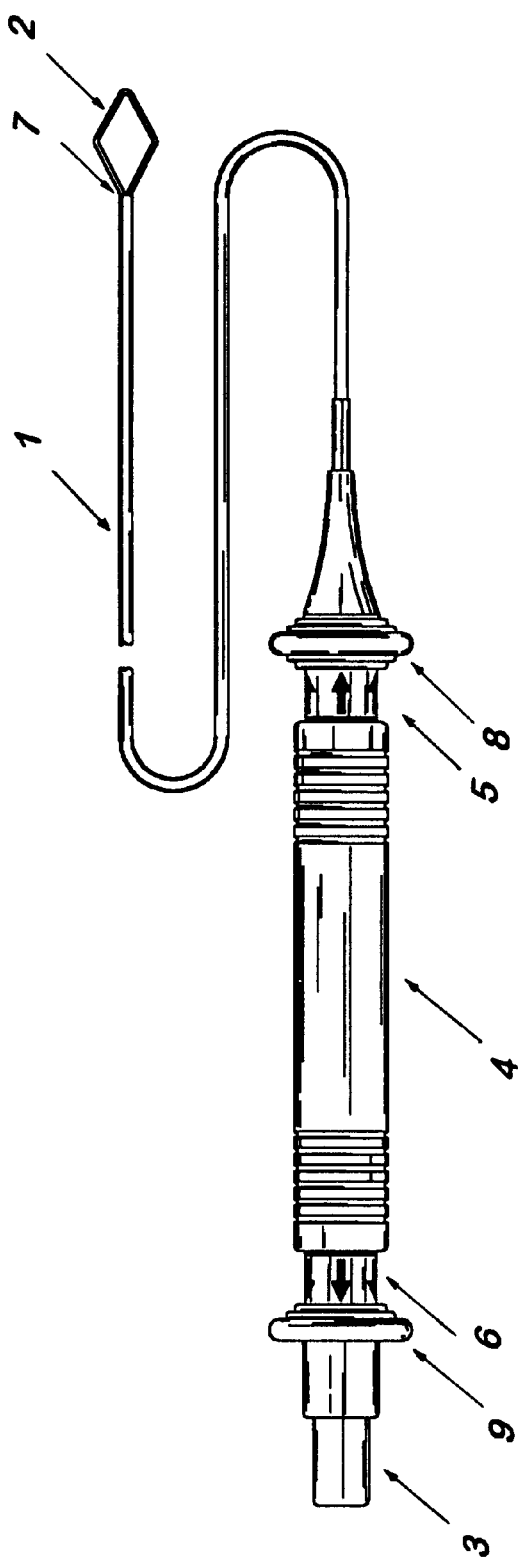
FIG. 1 is a prospective view of the steerable electrophysiology catheter having a loop electrode constructed in accordance with the principles of the present invention.

An electrophysiology catheter constructed in accordance with the principles of the present invention comprises: a catheter shaft having a distal tip section and a proximal section having a connector. FIG. 1 shows a prospective view of the catheter having a catheter shaft 1. The tip section has a loop electrode 2 and a hollow sheath 7 where the loop electrode can be retracted backward. The connector 3 at the proximal end of the catheter is part of the handle section 4. The handle has one steerable mechanism 5 and one retractable mechanism 6. The steerable mechanism 5 is to deflect the loop electrode when the loop electrode 2 is formed outside of the sheath 7. By pushing the front plunger 8 of the handle, the loop electrode deflects to one direction. By pulling the front plunger, the loop electrode either returns to its neutral position.

The retraction mechanism constitutes a flat wire which resists buckling inside the shaft 1 and the handle 4. In one embodiment, one end of the flat wire is soldered to the base of the tip section having a loop electrode while the other end is soldered onto the rear plunger 9. The rear plunger is used to push the tip section outwards of the sheath for ablation purpose. While the catheter is introduced into the body or removed from the body, the tip section comprising a loop electrode is retracted into the sheath 7 by pulling back the rear plunger.

Figure 2:
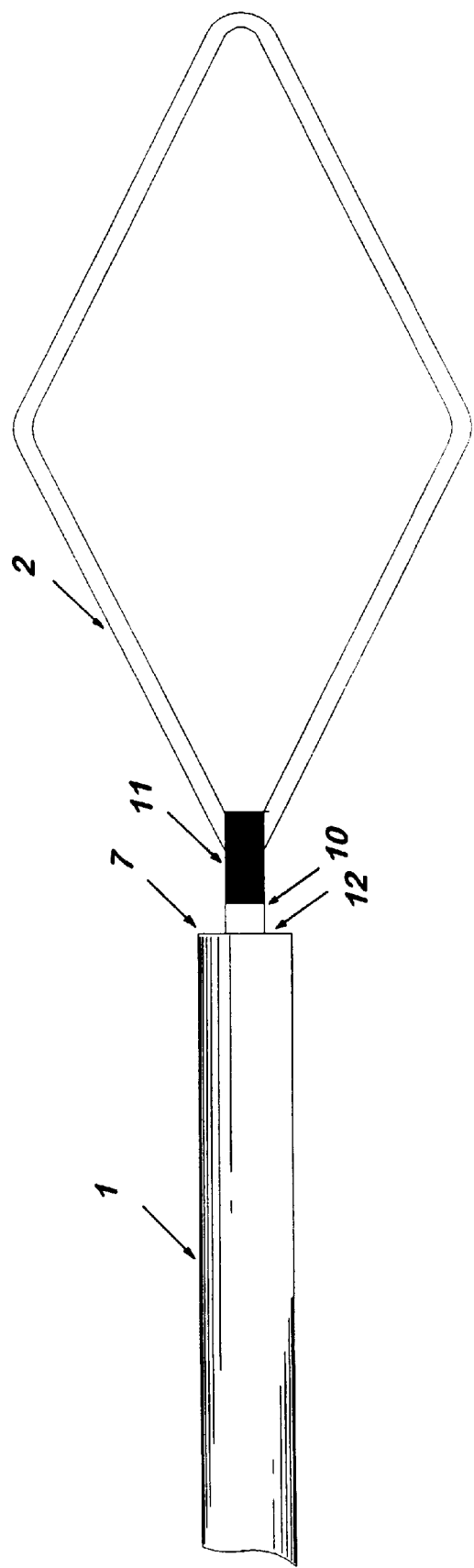
FIG. 2 is a close-up view of the tip section of the steerable catheter having a loop electrode.

FIG. 2 shows a close-up view of the tip section of FIG. 1. The tip section comprises a loop electrode 2. In one embodiment, the loop electrode is formed of a conducting material. The loop electrode is soldered to a flat wire 10 at the base 11 of the tip section. In another embodiment, the loop electrode is a spiral wire wrapped outside of the tubular loop shaft and forms a continuous loop. The spiral wire electrode has a conducting wire which is insulated, piercing through the tubing shaft into the lumen. Said conducting wire passes through the lumen and is soldered to a contact pin of the connector. The tip section having a spiral wire electrode or a loop electrode formed of conducting material can be extended out of the sheath and retracted into the sheath by a retraction mechanism at the handle. To prevent blood from backflow into the sheath 7, a silicone type stopper 12 is installed at the opening end of the sheath.

Figure 3:
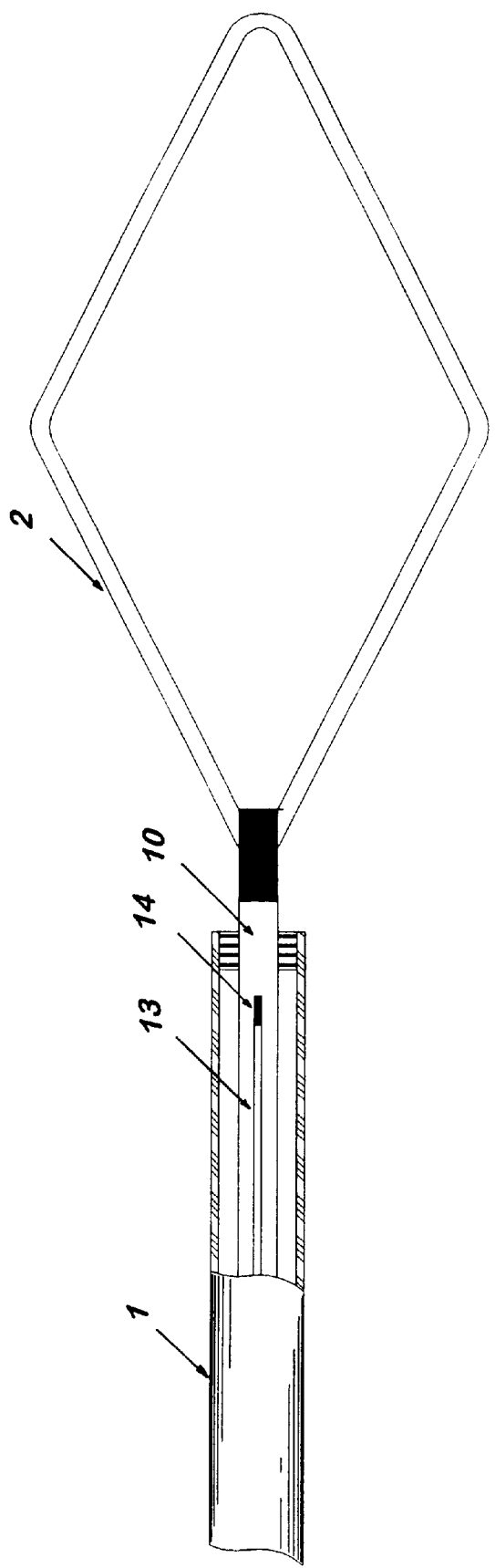
FIG. 3 a cross-sectional view of the tip section with one type of the steerable mechanism of FIG. 2.

FIG. 3 shows a cross-sectional view of the tip section with one type of steering mechanism. A steering wire 13 is firmly attached onto the flat wire 10 at the contact point 14. In this embodiment, the flat wire forms the skeleton of the loop electrode while a pliable plastic shaft covers over the flat wire. The metallic electrode, either a flexible meshed metal electrode, a flexible coiled metal electrode, a flexible coiled spring electrode, or a combination of the above, is placed outside of the plastic shaft. By pulling the steering wire 13 from the handle, the distal portion of the catheter shaft comprising a loop electrode shall deflect to one direction. By pulling another steering wire on the opposite side of the said flat wire, the loop electrode shall deflect to the opposite direction.

Figure 4:
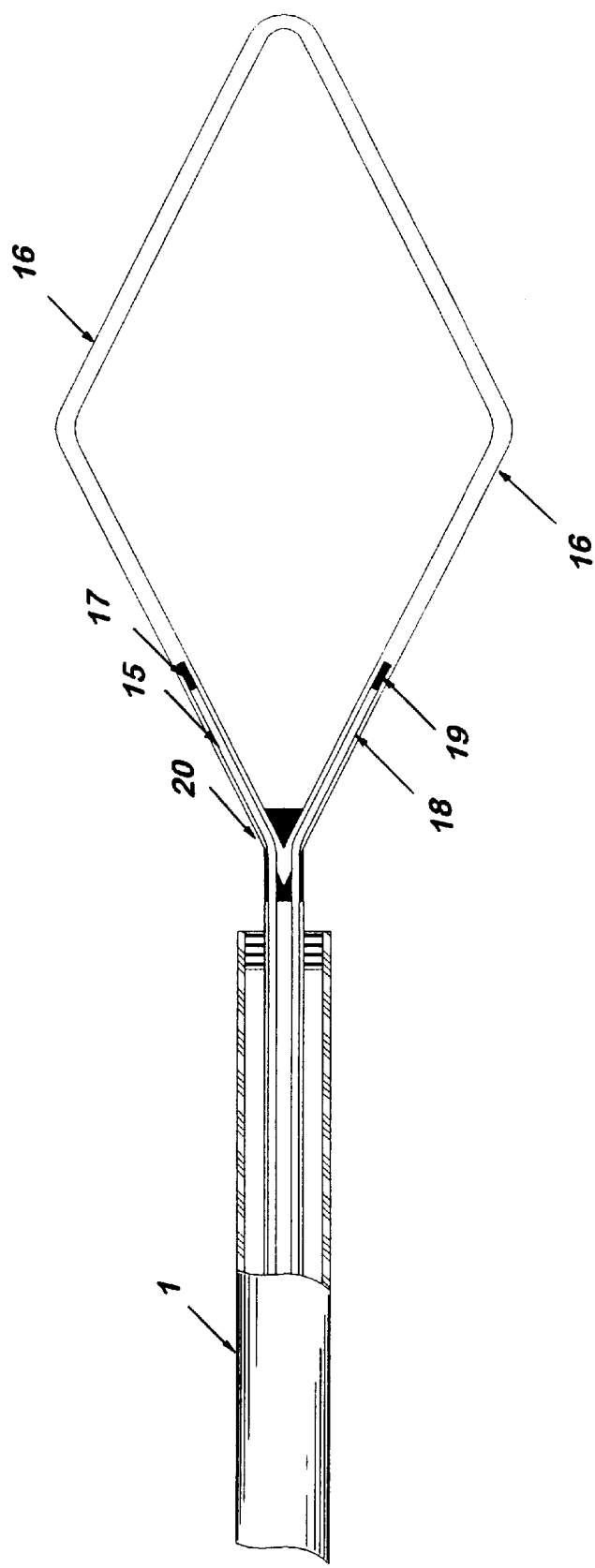
FIG. 4 is a cross-sectional view of the tip section with another type of the steerable mechanism of FIG. 2.

FIG. 4 shows a cross-sectional view of the tip section with an alternate steering mechanism. Two separate steering wires are extended into the branches of the loop electrode. One steering wire 15 is attached on the metal loop 16 at the soldered point 17. The second steering wire 18 is attached on the metal loop 16 at the soldered point 19. At the turning point 20, the steering wires 15 and 18 are elevated from the flat wire 16 so that the steering force pulls the loop electrode to deflect to one direction. To effect bi-directional deflection, another pair of steering wires can be attached on the opposite side of the flat wire 16 to yield the deflection to the opposite direction.

An insulated conducting wire from the loop electrode is connected to the contact pin of a connector at the proximal end of said catheter. The conducting wire from the connector end is externally connected to an EKG for diagnosis or to an RF generator during an electrophysiology ablation procedure. From there, the RF energy is transmitted through the conducting wire to the loop electrode and delivered the energy to the contact tissue. A temperature sensor, either a thermocouple or a thermister, is constructed for the loop electrode to measure the tissue contact temperature when RF energy is delivered. The temperature sensing wire from the thermocouple or thermister is connected to the contact pins of the connector and externally connected to a transducer and to a temperature controller. The temperature reading is thereafter relayed to a close-loop control mechanism to adjust the RF energy output. The RF energy delivered is thus controlled by the temperature sensor reading or by the pre-programmed control mechanism. In other embodiment where the loop electrode is formed of a conducting material, the insulated flat wire serves the same function as a conducting wire. RF energy can be transmitted to ablate the tissue through said flat wire.

From the foregoing, it should now be appreciated that an improved ablation electrophysiology catheter having a loop electrode and a steerable mechanism has been disclosed for electrophysiology ablation procedures. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A method for operating a steerable ablation catheter comprising a catheter shaft, which includes a distal tip section comprising a flat metal wire loop electrode; said flat metal wire loop electrode having a diamond shape; said catheter further including a proximal section having a handle and a catheter shaft section having a main central shaft lumen which extends from the handle to the distal tip section;

said catheter having first and second pairs of steering wires extending from the handle to the distal tip section through the main central shaft lumen;

said first pair of steering wires being connected to first and second solder points on a first face of the flat metal wire loop electrode;

said second pair of steering wires extending from the handle to the distal tip section through the main central shaft lumen and being connected to third and fourth solder points on a second face of the flat metal wire loop electrode;

wherein actuation of said first and second pairs of steering wires effects bi-directional deflection of the flat metal wire loop electrode; said method comprising the steps of:

A) percutaneously introducing the catheter through a blood vessel to the heart chamber B) deflecting the distal section of the catheter about a transverse axis to position the loop electrode near a target lesion on an interior wall of the heart chamber; and C) intimately contacting the loop electrode with the intracardiac cardiac tissue.

2. The method for operating an ablation catheter as in claim 1 further comprising applying microwave energy to the target locations through the loop electrode.

3. The method for operating an ablation catheter as in claim 1 further comprising applying ultrasound energy to the target locations through the loop electrode.

4. The method for operating an ablation catheter as in claim 1 further comprising applying radiofrequency energy to the target locations through the loop electrode.

5. An ablation catheter comprising a catheter shaft, which includes a distal tip section comprising a flat metal wire loop electrode; said flat metal wire loop electrode having a diamond shape; said catheter further including a proximal section having a handle and a catheter shaft section having a main central shaft lumen which extends from the handle to the distal tip section;

said catheter having first and second pairs of steering wires extending from the handle to the distal tip section through the main central shaft lumen;

said first pair of steering wires being connected to first and second solder points on a first face of the flat metal wire loop electrode;

said second pair of steering wires extending from the handle to the distal tip section through the main central shaft lumen and being connected to third and fourth solder points on a second face of the flat metal wire loop electrode;

wherein actuation of said first and second pairs of steering wires effects bi-directional deflection of the flat metal wire loop electrode.

* * * * *